United States Patent
Liang et al.

(10) Patent No.: US 10,947,586 B2
(45) Date of Patent: Mar. 16, 2021

(54) ADDITIVE COMPOSITION USED IN LAMP REACTION

(71) Applicant: Delta Electronics Int'l (Singapore) Pte Ltd, Singapore (SG)

(72) Inventors: Junxin Liang, Singapore (SG); Casthri Krishnamurthy, Singapore (SG); Shuwen An, Singapore (SG); Kah Sin Loh, Singapore (SG); Weishi Zhang, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 160 days.

(21) Appl. No.: 15/976,731

(22) Filed: May 10, 2018

(65) Prior Publication Data

US 2019/0218604 A1 Jul. 18, 2019

(30) Foreign Application Priority Data

Jan. 12, 2018 (SG) .......................... 10201800316R

(51) Int. Cl.
- C12Q 1/68 (2018.01)
- C12Q 1/6848 (2018.01)
- C12Q 1/6844 (2018.01)

(52) U.S. Cl.
CPC ......... *C12Q 1/6848* (2013.01); *C12Q 1/6844* (2013.01)

(58) Field of Classification Search
CPC ............ C12Q 1/6848; C12Q 2527/125; C12Q 1/6844; C12Q 2527/101; C12Q 2525/161
See application file for complete search history.

(56) References Cited

U.S. PATENT DOCUMENTS

| | | | | |
|---|---|---|---|---|
| 10,093,908 B2 * | 10/2018 | Piepenburg | .......... | C12Y 207/07 |
| 2014/0038174 A1 | 2/2014 | Fischer et al. | | |
| 2014/0193819 A1 * | 7/2014 | Hellyer | ............ | C12Q 2537/143 435/6.11 |
| 2017/0369929 A1 * | 12/2017 | Sitton | .................... | C12N 15/10 |

OTHER PUBLICATIONS

Watts et al. A loop-mediated isothermal amplification (LAMP) assay for Strongyloides stercoralis in stool that uses a visual detection method with SYTO-82 fluorescent dye. Am. J. Trop. Hyg. (2014) vol. 90, No. 2, pp. 306-311. (Year: 2014).*
Abbasi et al. Optimization of loop-mediated isothermal amplification (LAMP) assays for the detection of Leishmania DNA in human blood samples. Acta Tropica (2016) 162:20-26. (Year: 2016).*
Fukuta et al., "Development of Loop-Mediated Isothermal Amplification Assay for the Detection of Pythium Myriotylum" Letters in Applied Microbiology 59, 49-57, 2014.
Bhadra et al., "Real-Time Sequence-Validated Loop-Mediated Isothermal Amplification Assays for Detection of Middle East Respiratory Syndrome Coronavirus (MERS-CoV)", PLOS One | DOI:10.1371/journal.pone.0123126 Apr. 9, 2015.
Nose et al., "Polyethylene Glycol Accelerates Loop-Mediated Isothermal Amplification (LAMP) Reaction", Yakugaku Zasshi 133(10) 1121-1126 (2013).
Modak et al., "Rapid Point-of-Care Isothermal Amplification Assay for the Detection of Malaria without Nucleic Acid Purification", Infectious Diseases 2016; 9: 1-9.
Wang, D.-G et al., "Two Methods for Increased Specificity and Sensitivity in Loop-Mediated Isothermal Amplification", Molecules 2015, 20, 6048-6059.
Tong et al. (2011). Multiple strategies to improve sensitivity, speed and robustness of isothermal nucleic acid amplification for rapid pathogen detection. BMC biotechnology, 11(1), 50.
Watts et al. (2014). A loop-mediated isothermal amplification (LAMP) assay for Strongyloides stercoralis in stool that uses a visual detection method with SYTO-82 fluorescent dye. The American journal of tropical medicine and hygiene, 90 (2), 306-311.

* cited by examiner

*Primary Examiner* — David C Thomas
(74) *Attorney, Agent, or Firm* — Kirton McConkie; Evan R. Witt

(57) ABSTRACT

An additive composition used in a loop mediated isothermal amplification (LAMP) reaction for reducing a threshold time for a positive sample includes but not limited to EDTA, EGTA, BSA, DMSO, nonionic surfactants, and polymers, and the additive composition used in LAMP reactions includes at least one of the above mentioned additives and may be any combination use of the additives.

29 Claims, 23 Drawing Sheets

ADDITIVE COMPOSITION USED IN LAMP REACTION

FIELD OF THE INVENTION

The present invention relates to an additive composition used in nucleic acid amplification, and more particularly to an additive composition used in LAMP reaction.

BACKGROUND OF THE INVENTION

Polymerase Chain Reaction (PCR) has been extensively used in many areas for more than 30 years. Isothermal nucleic acid amplification techniques are ideal complements for PCR in molecular diagnostic applications because they do not require thermal cycling. Loop mediated isothermal amplification (LAMP) is one of the most widely used isothermal DNA amplification techniques with high potential for molecular diagnostics due to its high specificity, high amplification efficiency, robustness, and low cost. Basically, LAMP is an auto-cycling strand displacement DNA amplification performed by a DNA polymerase with high strand displacement activity.

In real-time LAMP, the time for a positive reaction to reach above a threshold is known as time to threshold (TTT) or time to result (TTR). This term may be interpreted as a term similar to Ct, the threshold cycle number in real-time PCR. Although TTT varies considerably depending on the target type and concentration, primers, type of sample matrix, and the real-time detection method, it provides a quantitative measure of LAMP assay performance.

Generally, with its high amplification efficiency, LAMP can amplify DNA $10^9$-$10^{10}$ times in 15-60 minutes. LAMP uses 4-6 primers to recognize 6-8 distinct regions of target DNA, which makes it much more specific in target detection compared to most other isothermal DNA amplification techniques. However, there are still some drawbacks and disadvantages of the current LAMP reactions. FIGS. 1A and 1B show examples of amplification curves from literatures (Fukuta et al., "Development of Loop-Mediated Isothermal Amplification Assay for the Detection of Pythium Myriotylum"; Bhadra et al., "Real-Time Sequence-Validated Loop-Mediated Isothermal Amplification Assays for Detection of Middle East Respiratory Syndrome Coronavirus (MERS-CoV)"). Due to the intrinsic property of the DNA polymerase used, certain level of template-independent background amplification is still very likely to occur in LAMP. The amplification curves of negative samples are not always 'flat', indicating the existence of non-specific background amplification, as shown in FIG. 1A. Besides, when the reaction time is long enough, even negative samples are very likely to amplify, resulting a TTT similar to those of low-copy templates, as shown in FIG. 1B, in which case detection of the low-copy template is not reliable.

Hence, goals for LAMP optimization are to obtain a faster TTT for positive samples, which means increased reaction speed, and slower TTT for negative controls, which means lower background signals and decreased non-specific amplification. Eventually consistent detection of low copy template can be realized through an increased separation between positive and negative TTT. Multiple factors should be assessed for LAMP optimization, which include primers (design, concentration and ratio), enzyme (type and concentration), reaction temperature, concentration of ions in buffer (especially $Mg^{2+}$), reaction pH, and additives.

For years, various additives and enhancing agents have been studied and used in PCR to increase the amplification product yield, specificity and consistency of reactions. Recently, there have been a few studies of applying additives in isothermal reactions. In a research article in 2013 (Nose et al., "Polyethylene Glycol Accelerates Loop-Mediated Isothermal Amplification (LAMP) Reaction"), polyethylene glycol (PEG) was reported to accelerate LAMP reaction, but only single additive was used so the effect of combinational use of PEG with other additives in LAMP is unknown, and the common problem of non-specific background amplification of primers in LAMP was not identified and solved. In one research paper in 2015 (Modak et al., "Rapid Point-of-Care Isothermal Amplification Assay for the Detection of Malaria without Nucleic Acid Purification"), bovine serum albumin (BSA) was used to facilitate LAMP reaction in the presence of blood inhibitors for the detection of Malaria without nucleic acid purification, but the potentially generalized use of BSA as a common enhancer in standard LAMP with or without inhibitors was not illustrated, and again the common problem of non-specific background amplification in LAMP was not identified in this paper. In another research paper in 2015 (Wang, D.-G et al., "Two Methods for Increased Specificity and Sensitivity in Loop-Mediated Isothermal Amplification"), DMSO was reported to increase the specificity and sensitivity in prfA LAMP assay for Listeria monocytogenes detection, however, the effect of combinational use of DMSO with other additives in LAMP is unknown.

Thus, there is a need of providing additive compositions for enhancing LAMP reactions to overcome the drawbacks of the prior arts.

SUMMARY OF THE INVENTION

An object of the present invention is to provide various additive compositions for enhancing LAMP reactions, particularly reducing threshold time of positive samples, reducing template-independent background amplification of primers, and allowing a consistent detection of low copy number of target DNA.

According to an aspect of the present invention, there is provided an additive composition used in a loop mediated isothermal amplification (LAMP) reaction for reducing a threshold time for a positive sample. The additive composition comprises a first additive and a second additive. The first additive is selected from the group consisting of ethylenediaminetetraacetic acid (EDTA), ethylene glycol tetraacetic acid (EGTA) and a combination thereof. The second additive is selected from the group consisting of bovine serum albumin (BSA), dimethyl sulfoxide (DMSO), nonionic surfactants, polymers and a combination thereof.

In an embodiment of the present invention, a concentration of EDTA is 0.1-1.5 mM.

In an embodiment of the present invention, a concentration of EGTA is 0.1-3 mM.

In an embodiment of the present invention, a concentration of BSA is 0.5-10% (w/v).

In an embodiment of the present invention, a concentration of DMSO is 0.5-7% (v/v).

In an embodiment of the present invention, the nonionic surfactants include Tween-20, Tween-21, Tween-40, Tween-60, Tween-61, Tween-65, Tween-80, Span 20, Span 40, Span 60, Span 80, Span 83, Span 85 and Span 120.

In an embodiment of the present invention, a concentration of the nonionic surfactant is 0.5-6% (v/v).

In an embodiment of the present invention, the polymers include polyethylene glycol (PEG), polyvinylpyrrolidone (PVP), Dextran and Ficoll.

In an embodiment of the present invention, PEG includes PEG200 and PEG8000.

In an embodiment of the present invention, a concentration of PEG200 is 0.5-8% (v/v), and a concentration of PEG8000 is 0.5-6% (w/v).

In an embodiment of the present invention, a concentration of PVP is 0.5-10% (w/v).

In an embodiment of the present invention, a concentration of Dextran is 0.5-5% (w/v).

In an embodiment of the present invention, a concentration of Ficoll is 0.5-8% (w/v).

According to another aspect of the present invention, there is provided an additive composition used in a loop mediated isothermal amplification (LAMP) reaction for reducing a threshold time for a positive sample. The additive composition comprises a first additive and a second additive. The first additive is selected from the group consisting of polyethylene glycol (PEG), polyvinylpyrrolidone (PVP), Dextran and Ficoll and a combination thereof. The second additive is selected from the group consisting of bovine serum albumin (BSA), dimethyl sulfoxide (DMSO), nonionic surfactants and a combination thereof.

According to an additional aspect of the present invention, there is provided an additive composition used in a loop mediated isothermal amplification (LAMP) reaction for reducing a threshold time for a positive sample. The additive composition comprises a single additive selected from the group consisting of ethylene glycol tetraacetic acid (EGTA), polyvinylpyrrolidone (PVP), Dextran, Ficoll and Tween-80.

In an embodiment of the present invention, a concentration of Tween-80 is 0.5-5% (v/v).

The above objects and advantages of the embodiments of the present invention become more readily apparent to those ordinarily skilled in the art after reviewing the following detailed description and accompanying drawings, in which:

DETAILED DESCRIPTION OF THE PREFERRED EMBODIMENT

Figure 1A:
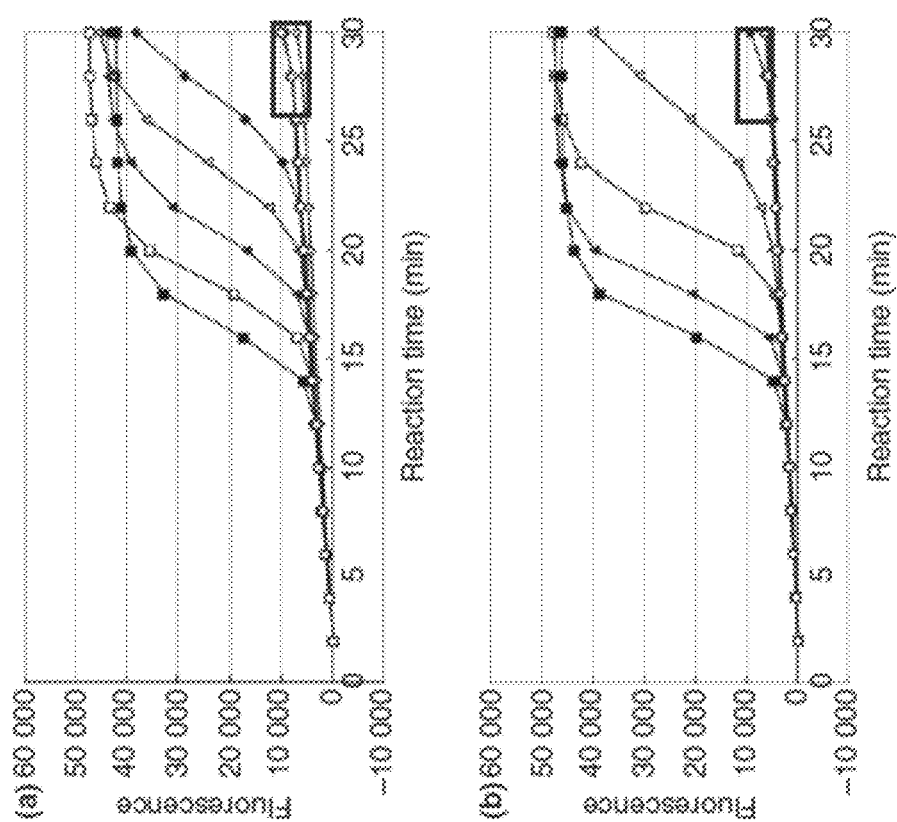
FIGS. 1A and 1B show examples of amplification curves from literatures.
Figure 1B:
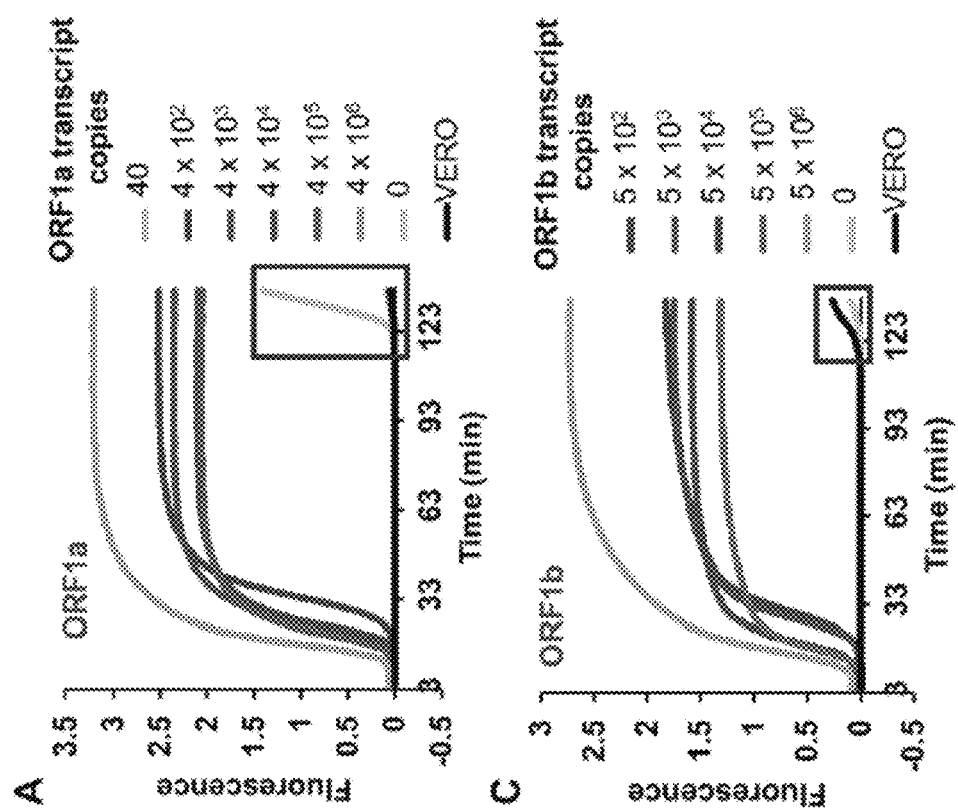

The present invention will now be described more specifically with reference to the following embodiments. It is to be noted that the following descriptions of the embodiments of this invention are presented herein for purpose of illustration and description only; it is not intended to be exhaustive or to be limited to the precise form disclosed.

In order to reduce threshold time for positive samples and template-independent background amplification in standard LAMP reactions, the present invention tested various compositions of individual additive or a combination of additives in standard LAMP reaction solutions. The additive may include but not limited to ethylenediaminetetraacetic acid (EDTA), ethylene glycol tetraacetic acid (EGTA), bovine serum albumin (BSA), dimethyl sulfoxide (DMSO), and nonionic surfactants, such as Tween-20, Tween-21, Tween-40, Tween-60, Tween-61, Tween-65, Tween-80, Span 20, Span 40, Span 60, Span 80, Span 83, Span 85 and Span 120. The additive may also include polymers, such as but not limited to polyethylene glycol (PEG) (for example, PEG200 and PEG8000), polyvinylpyrrolidone (PVP), Dextran and Ficoll.

LAMP reactions were set up using 6 primers (1.6 µM FIP and BIP, and 0.2 µM F3 and B3, and 0.4 µLF and LB) plus certain number of copies of plasmid DNA containing target sequence in a buffer containing 20 mM Tris, pH 8.8 (25° C.), 50 mM KCl, 10 mM $(NH_4)_2SO_4$, 2 mM $MgSO_4$, and 0.1% (v/v) Tween-20, supplemented with additional 6 mM MgSO$_4$, 1.4 mM dNTPs, and optional additive composition. Reactions were all 25 μl, contained 8 U Bst polymerase (NEB M0538L), and were incubated at 67.4° C. Fluorescence signal was read every one minute. Threshold time was defined by fluorescence measurement in Bio-Rad CFX96™ with presence of EvaGreen dye (Biotium). All the additives were tested with a primer set targeting a specific region of OprL gene. The effect, working range and optimal concentration may be different for different targets and primers.

In an embodiment, EDTA was used as an individual additive, and the tested concentration was up to 2 mM. It was found that the use of EDTA can shorten the threshold time of LAMP in a concentration range of 0.1-1.5 mM, preferably 0.5-1 mM.

In an embodiment, EGTA was used as an individual additive, and the tested concentration was up to 3 mM. It was found that the use of EGTA can shorten the threshold time of LAMP in a concentration range of 0.1-3 mM, preferably 1-2 mM.

In an embodiment, BSA was used as an individual additive, and the tested concentration was up to 10% (w/v). It was found that the use of BSA can shorten the threshold time of LAMP in a concentration range of 0.5-10% (w/v), preferably 2-4% (w/v).

In an embodiment, DMSO was used as an individual additive, and the tested concentration was up to 7% (v/v). It was found that the use of DMSO can shorten the threshold time of LAMP in a concentration range of 0.5-7% (v/v), preferably 2-5% (v/v).

In an embodiment, Tween-20 was used as an individual additive, and the tested concentration was up to 6% (v/v). It was found that the use of Tween-20 can shorten the threshold time of LAMP in a concentration range of 0.5-6% (v/v), preferably 3-6% (v/v).

In an embodiment, PEG200 was used as an individual additive, and the tested concentration was up to 8% (v/v). It was found that the use of PEG200 can shorten the threshold time of LAMP in a concentration range of 0.5-8% (v/v), preferably 3-6% (v/v).

In an embodiment, PEG8000 was used as an individual additive, and the tested concentration was up to 6% (w/v). It was found that the use of PEG8000 can shorten the threshold time of LAMP in a concentration range of 0.5-6% (w/v), preferably 2-6% (w/v).

In an embodiment, PVP40 (MW: about 40K) was used as an individual additive, and the tested concentration was up to 10% (w/v). It was found that the use of PVP40 can shorten the threshold time of LAMP in a concentration range of 0.5-10% (w/v), preferably 5-7% (w/v).

Figure 2:
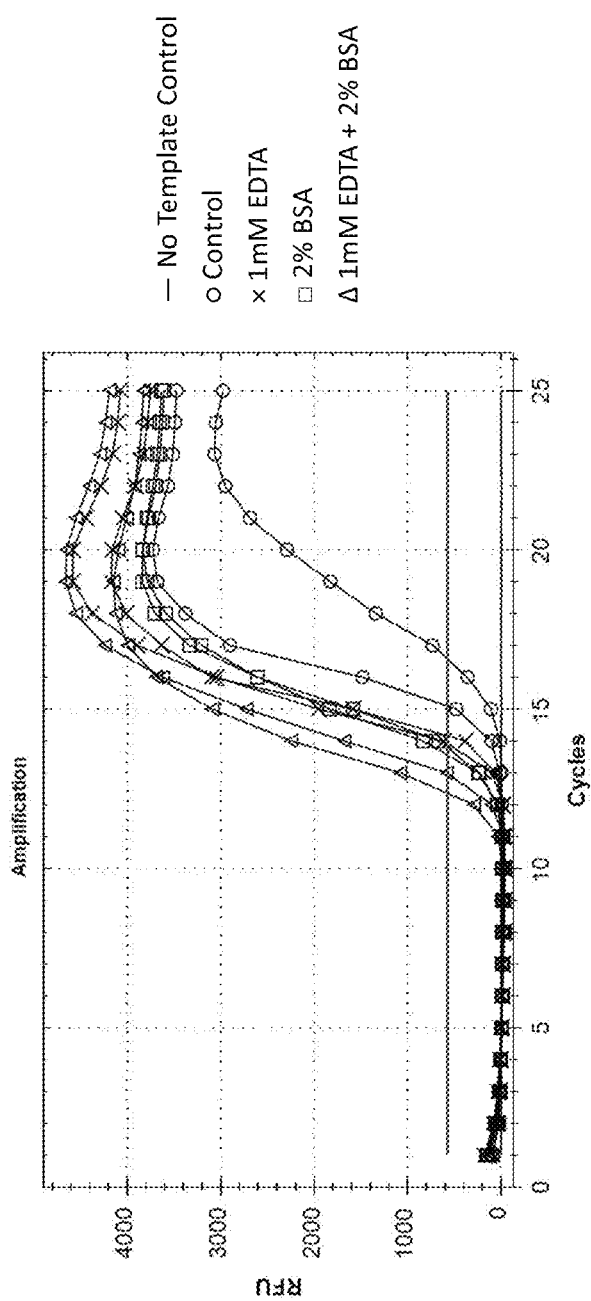
FIG. 2 shows the effects of individual or combination use of EDTA and BSA in LAMP reactions according to an embodiment of the present invention.

In an embodiment, EDTA and BSA were used as a combination of additives, wherein the concentration of EDTA is 1 mM and the concentration of BSA is 2% (w/v). As shown in FIG. 2, the combination use of EDTA and BSA can significantly shorten the threshold time of LAMP, and the effect is better than the single use of EDTA or BSA.

Figure 3:
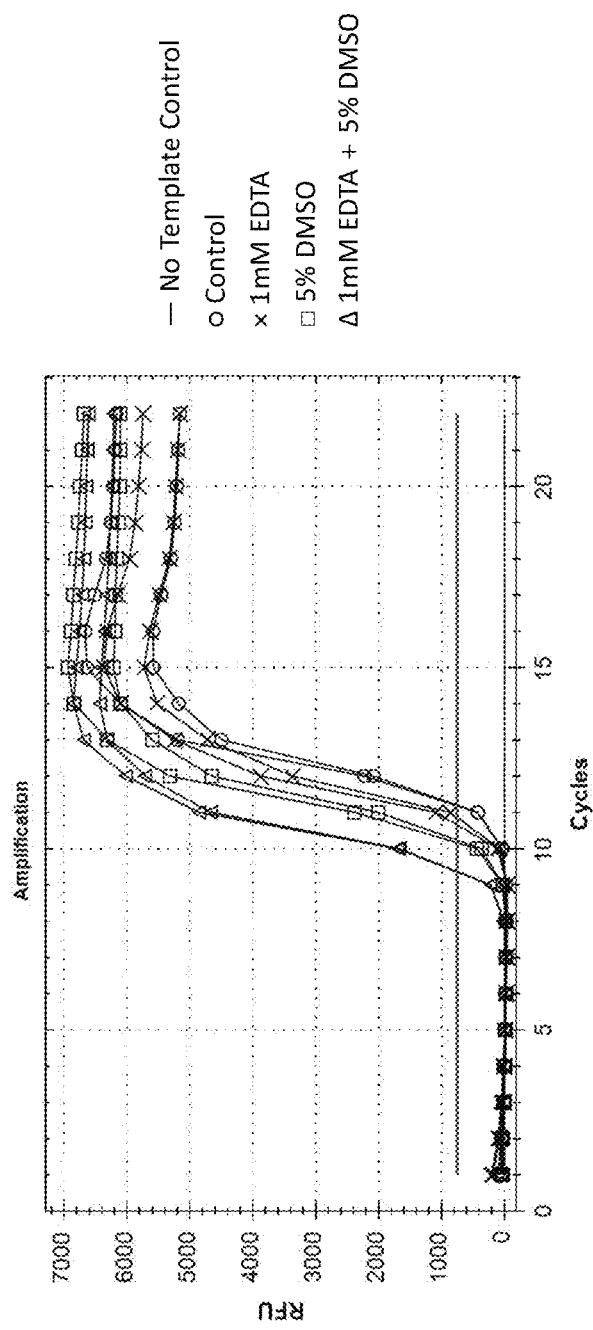
FIG. 3 shows the effects of individual or combination use of EDTA and DMSO in LAMP reactions according to an embodiment of the present invention.

In an embodiment, EDTA and DMSO were used as a combination of additives, wherein the concentration of EDTA is 1 mM and the concentration of DMSO is 5% (v/v). As shown in FIG. 3, the combination use of EDTA and DMSO can significantly shorten the threshold time of LAMP, and the effect is better than the single use of EDTA or DMSO.

Figure 4:
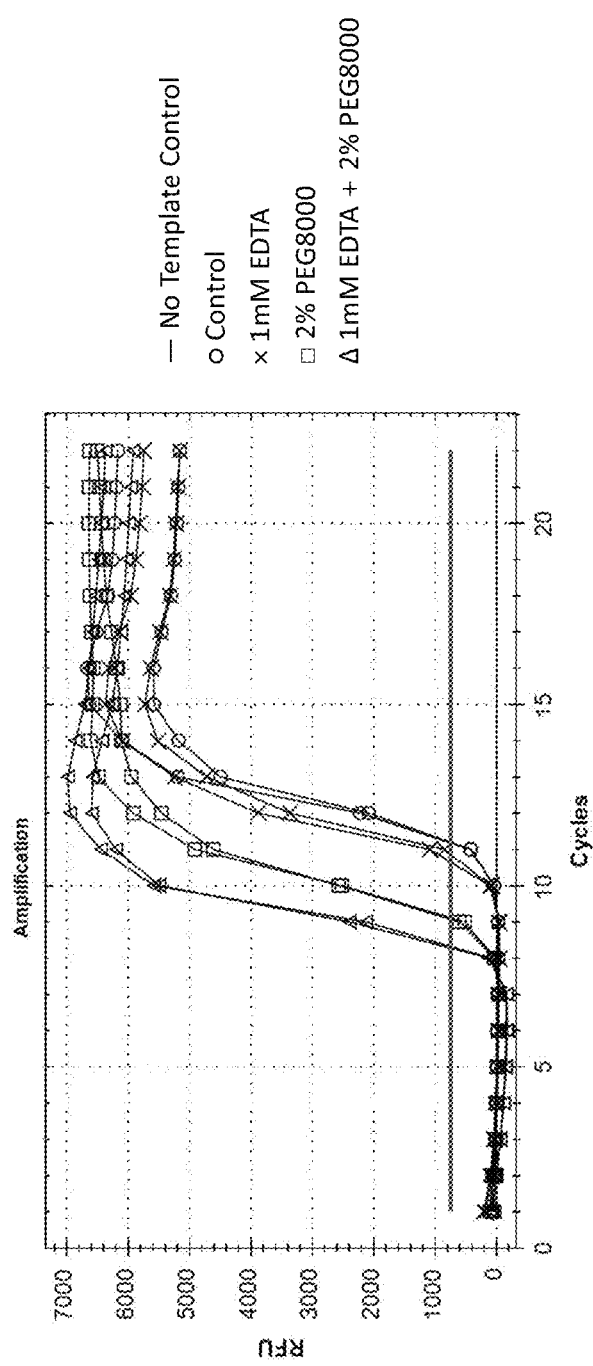
FIG. 4 shows the effects of individual or combination use of EDTA and PEG8000 in LAMP reactions according to an embodiment of the present invention.

In an embodiment, EDTA and PEG8000 were used as a combination of additives, wherein the concentration of EDTA is 1 mM and the concentration of PEG8000 is 2% (w/v). As shown in FIG. 4, the combination use of EDTA and PEG8000 can significantly shorten the threshold time of LAMP, and the effect is better than the single use of EDTA or PEG8000.

Figure 5:
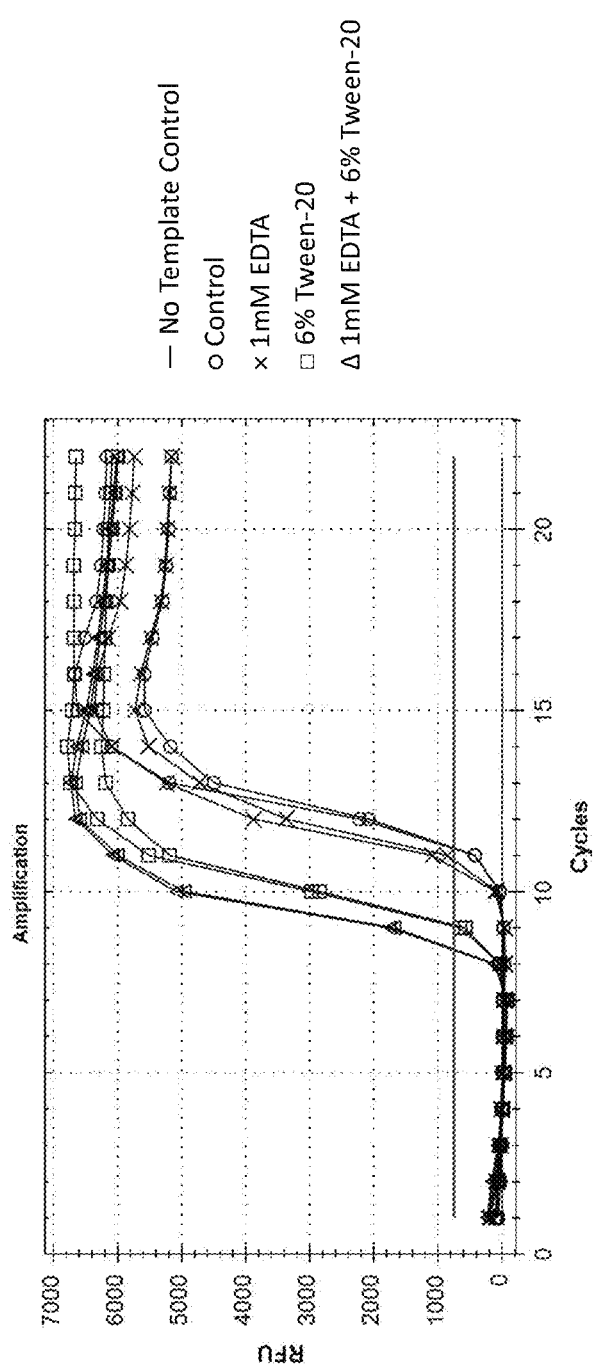
FIG. 5 shows the effects of individual or combination use of EDTA and Tween-20 in LAMP reactions according to an embodiment of the present invention.

In an embodiment, EDTA and Tween-20 were used as a combination of additives, wherein the concentration of EDTA is 1 mM and the concentration of Tween-20 is 6% (v/v). As shown in FIG. 5, the combination use of EDTA and Tween-20 can significantly shorten the threshold time of LAMP, and the effect is better than the single use of EDTA or Tween-20.

Figure 6:
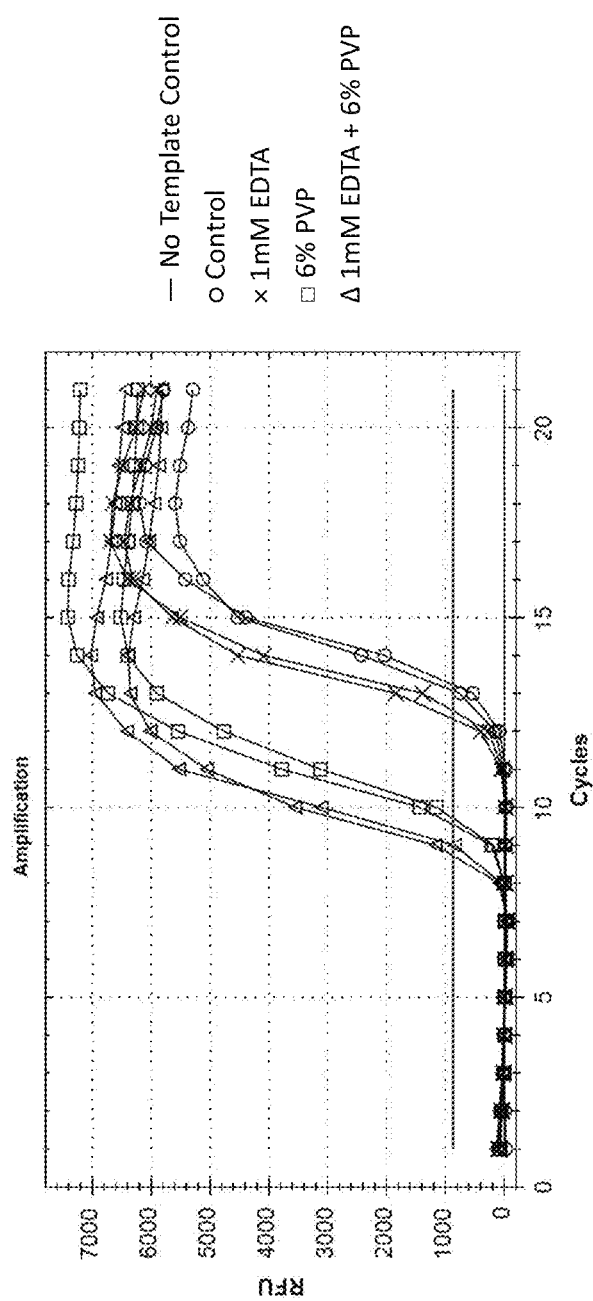
FIG. 6 shows the effects of individual or combination use of EDTA and PVP in LAMP reactions according to an embodiment of the present invention.

In an embodiment, EDTA and PVP were used as a combination of additives, wherein the concentration of EDTA is 1 mM and the concentration of PVP is 6% (w/v). As shown in FIG. 6, the combination use of EDTA and PVP can significantly shorten the threshold time of LAMP, and the effect is better than the single use of EDTA or PVP.

Figure 7:
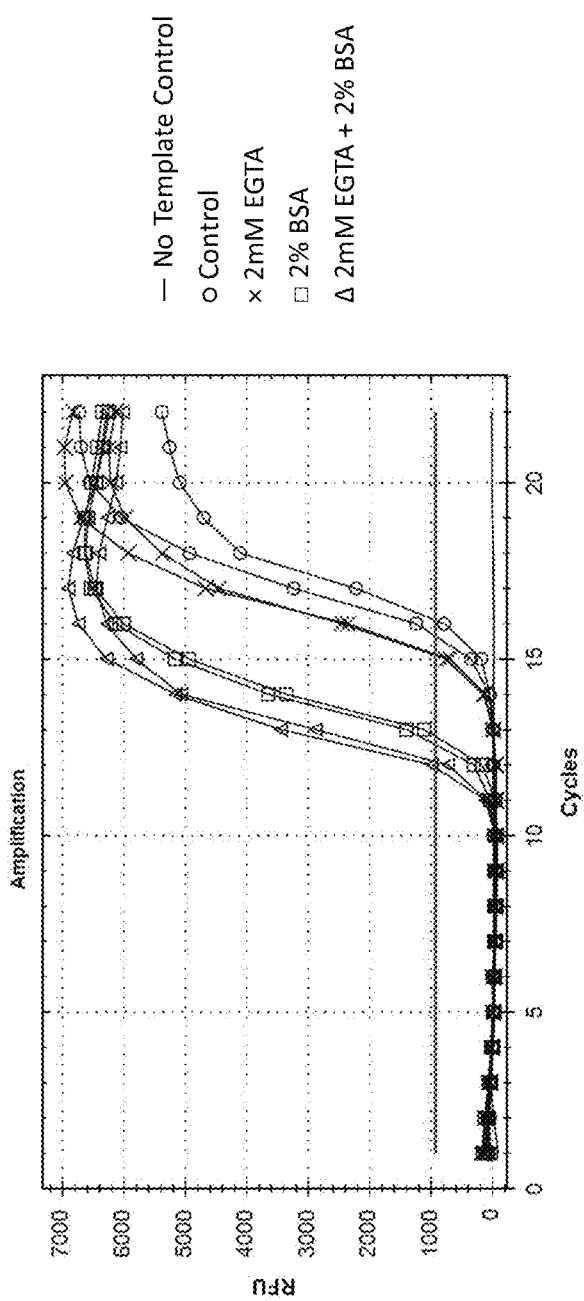
FIG. 7 shows the effects of individual or combination use of EGTA and BSA in LAMP reactions according to an embodiment of the present invention.

In an embodiment, EGTA and BSA were used as a combination of additives, wherein the concentration of EGTA is 2 mM and the concentration of BSA is 2% (w/v). As shown in FIG. 7, the combination use of EGTA and BSA can significantly shorten the threshold time of LAMP, and the effect is better than the single use of EGTA or BSA.

Figure 8:
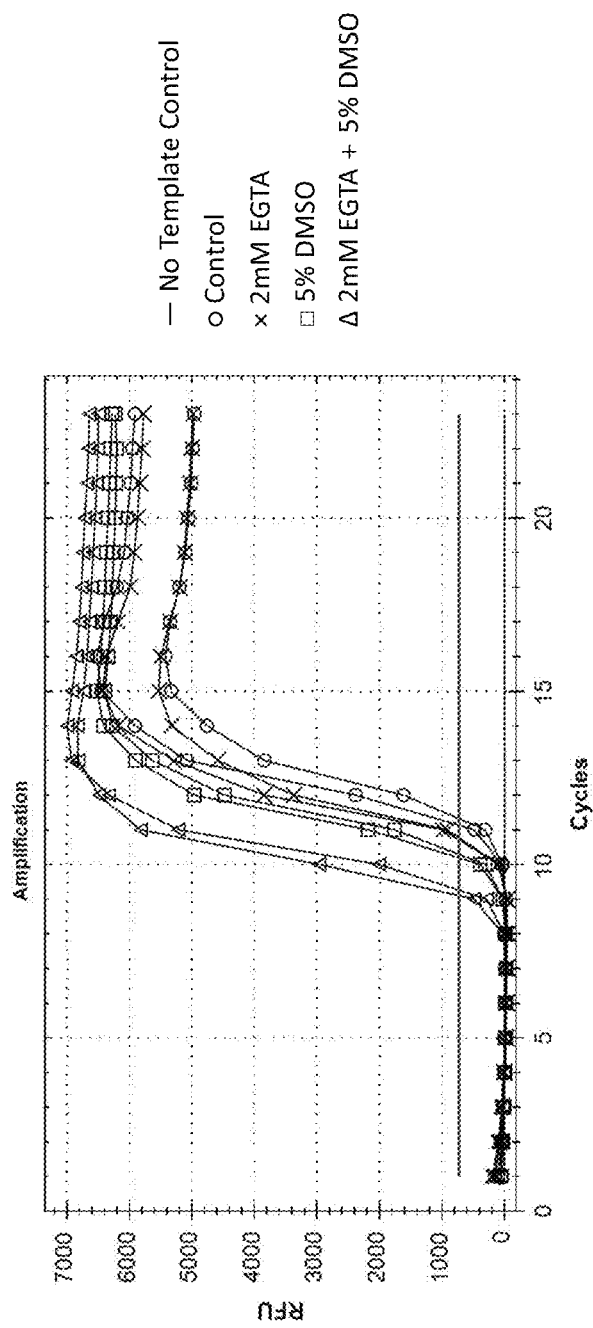
FIG. 8 shows the effects of individual or combination use of EGTA and DMSO in LAMP reactions according to an embodiment of the present invention.

In an embodiment, EGTA and DMSO were used as a combination of additives, wherein the concentration of EGTA is 2 mM and the concentration of DMSO is 5% (v/v). As shown in FIG. 8, the combination use of EGTA and DMSO can significantly shorten the threshold time of LAMP, and the effect is better than the single use of EGTA or DMSO.

Figure 9:
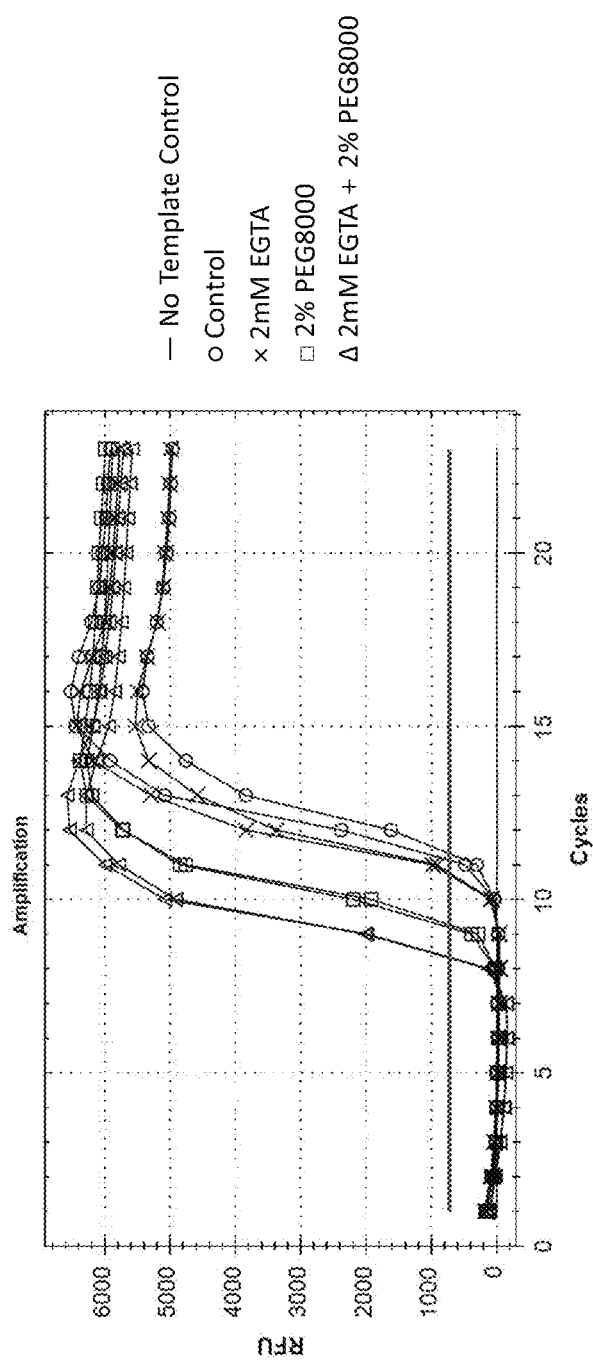
FIG. 9 shows the effects of individual or combination use of EGTA and PEG8000 in LAMP reactions according to an embodiment of the present invention.

In an embodiment, EGTA and PEG8000 were used as a combination of additives, wherein the concentration of EGTA is 2 mM and the concentration of PEG8000 is 2% (w/v). As shown in FIG. 9, the combination use of EGTA and PEG8000 can significantly shorten the threshold time of LAMP, and the effect is better than the single use of EGTA or PEG8000.

Figure 10:
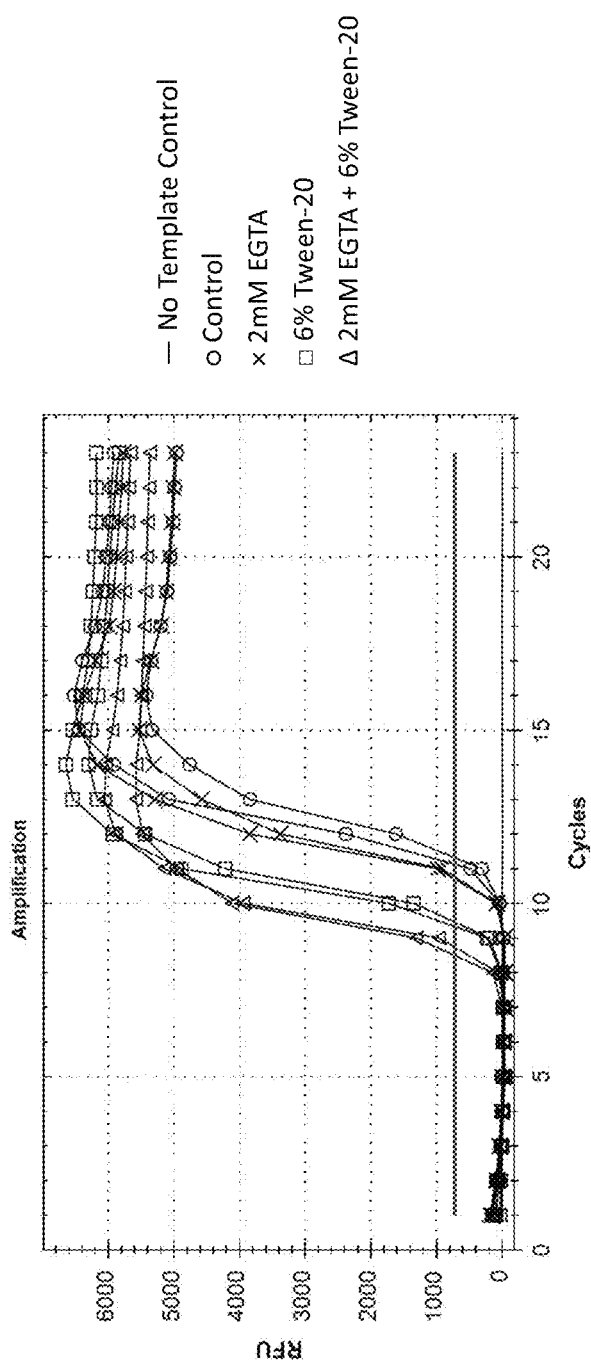
FIG. 10 shows the effects of individual or combination use of EGTA and Tween-20 in LAMP reactions according to an embodiment of the present invention.

In an embodiment, EGTA and Tween-20 were used as a combination of additives, wherein the concentration of EGTA is 2 mM and the concentration of Tween-20 is 6% (v/v). As shown in FIG. 10, the combination use of EGTA and Tween-20 can significantly shorten the threshold time of LAMP, and the effect is better than the single use of EGTA or Tween-20.

Figure 11:
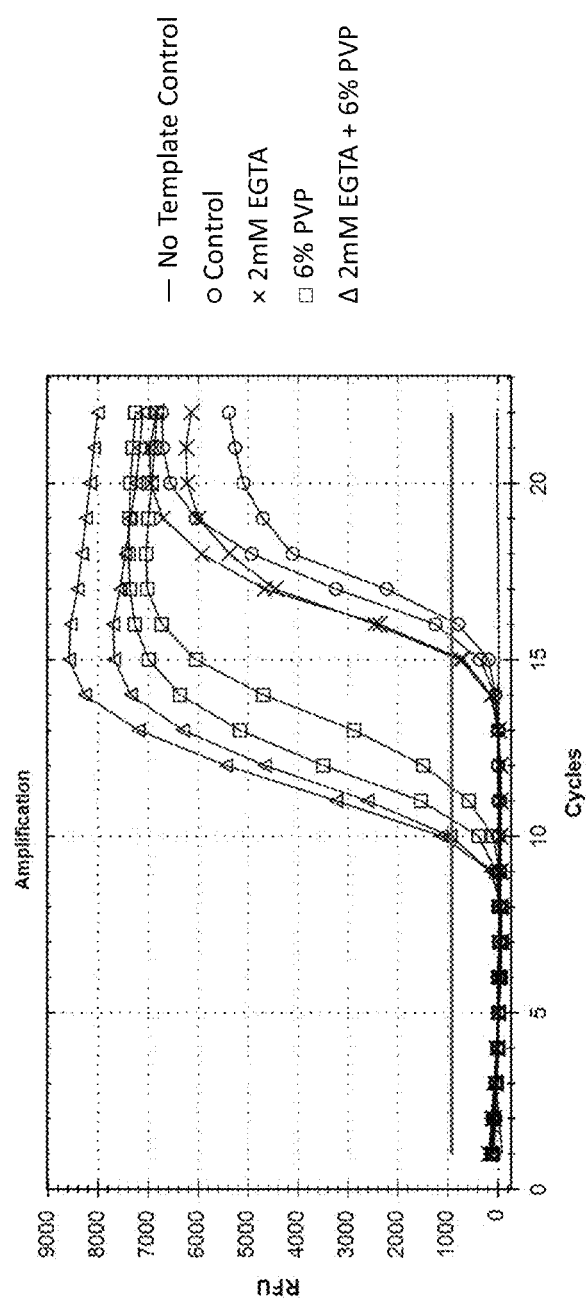
FIG. 11 shows the effects of individual or combination use of EGTA and PVP in LAMP reactions according to an embodiment of the present invention.

In an embodiment, EGTA and PVP were used as a combination of additives, wherein the concentration of EGTA is 2 mM and the concentration of PVP is 6% (w/v). As shown in FIG. 11, the combination use of EGTA and PVP can significantly shorten the threshold time of LAMP, and the effect is better than the single use of EGTA or PVP.

Figure 12:
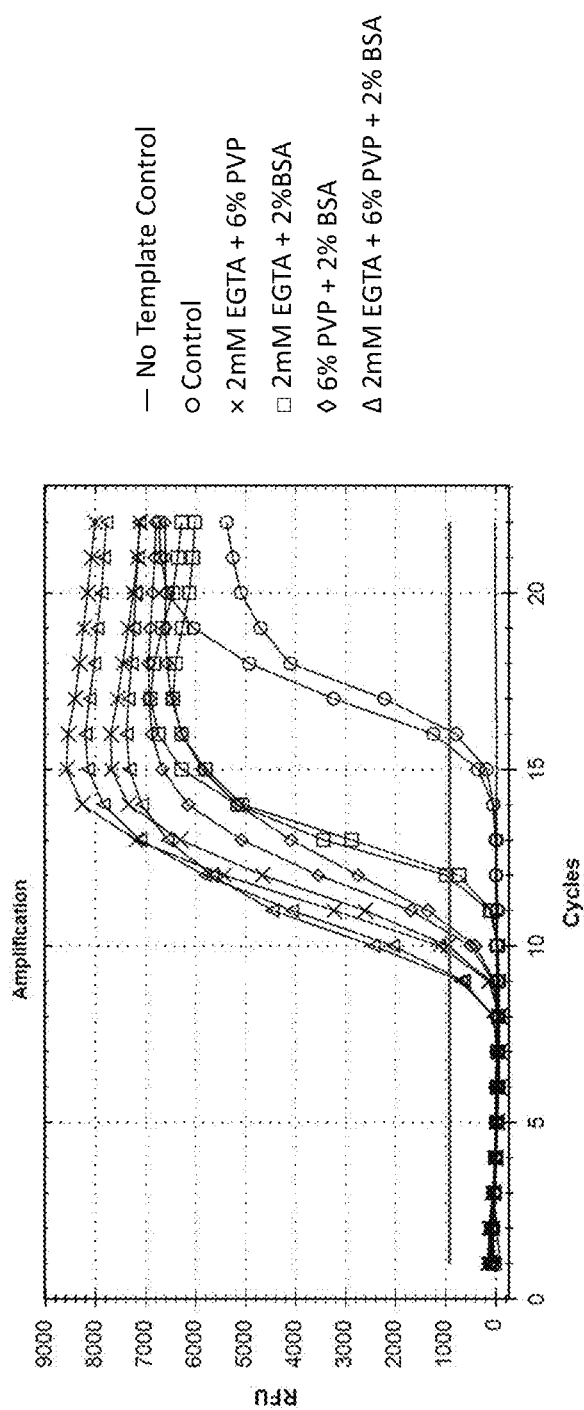
FIG. 12 shows the effects of combination use of EGTA, PVP and BSA in LAMP reactions according to an embodiment of the present invention.

In an embodiment, EGTA, BSA and PVP were used as a combination of additives, wherein the concentration of EGTA is 2 mM, the concentration of BSA is 2% (w/v), and the concentration of PVP is 6% (w/v). As shown in FIG. 12, the combination use of EGTA, BSA and PVP can significantly shorten the threshold time of LAMP, and the effect is better than the single use of EGTA, BSA or PVP, or the combination use of EGTA+BSA, PVP+BSA, or PVP+EGTA.

Figure 13:
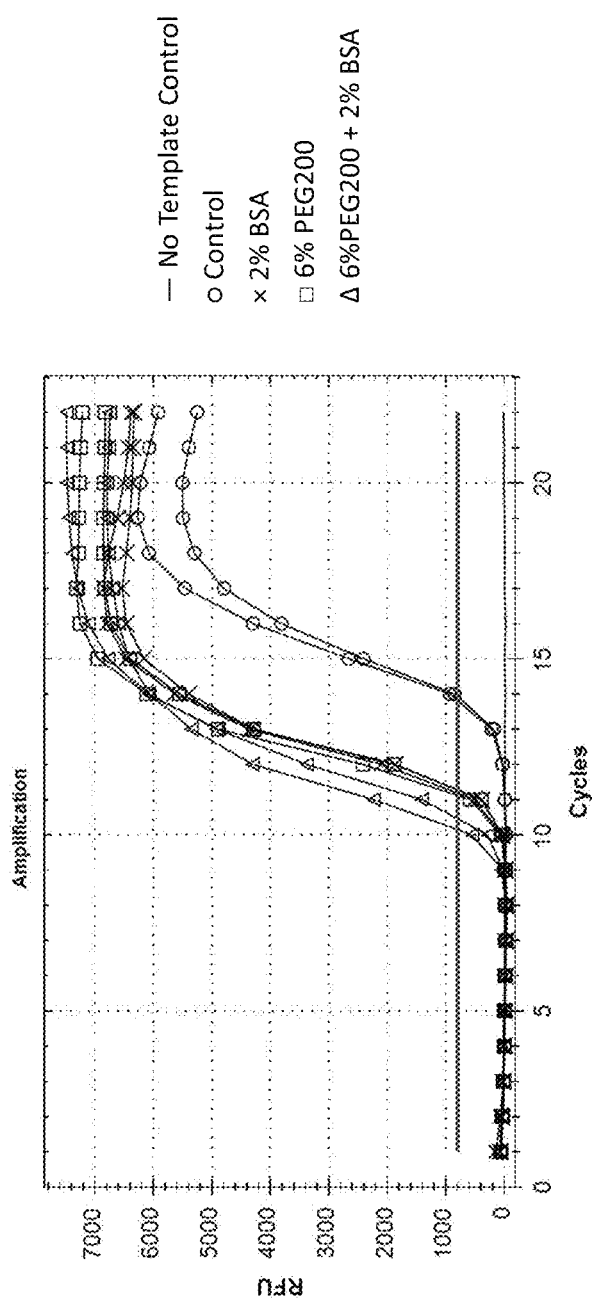
FIG. 13 shows the effects of individual or combination use of PEG200 and BSA in LAMP reactions according to an embodiment of the present invention.

In an embodiment, PEG200 and BSA were used as a combination of additives, wherein the concentration of PEG200 is 6% (v/v) and the concentration of BSA is 2% (w/v). As shown in FIG. 13, the combination use of PEG200 and BSA can significantly shorten the threshold time of LAMP, and the effect is better than the single use of PEG200 or BSA.

Figure 14:
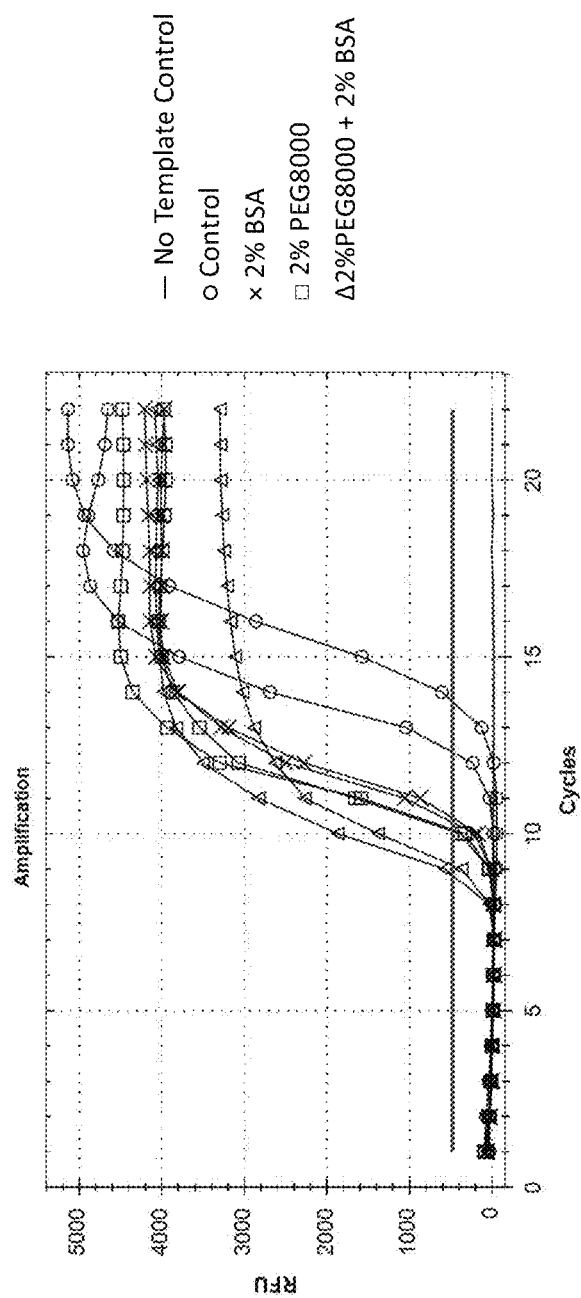
FIG. 14 shows the effects of individual or combination use of PEG8000 and BSA in LAMP reactions according to an embodiment of the present invention.

In an embodiment, PEG8000 and BSA were used as a combination of additives, wherein the concentration of PEG8000 is 2% (w/v) and the concentration of BSA is 2% (w/v). As shown in FIG. 14, the combination use of PEG8000 and BSA can significantly shorten the threshold time of LAMP, and the effect is better than the single use of PEG8000 or BSA.

Figure 15:
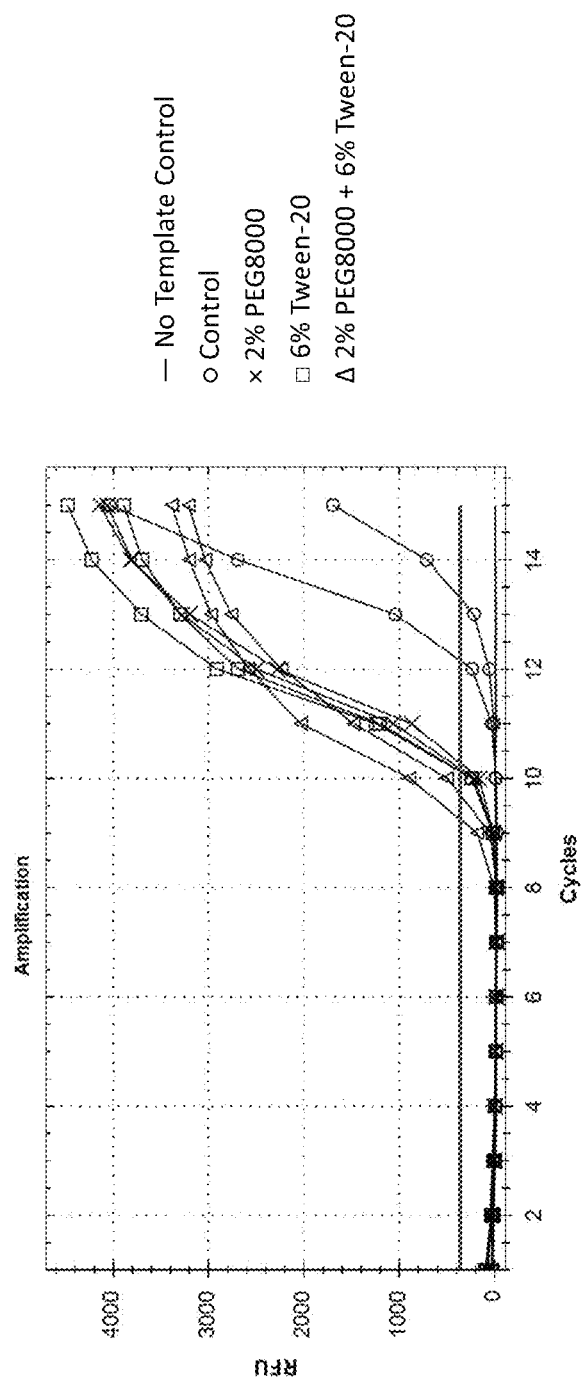
FIG. 15 shows the effects of individual or combination use of PEG8000 and Tween-20 in LAMP reactions according to an embodiment of the present invention.

In an embodiment, PEG8000 and Tween-20 were used as a combination of additives, wherein the concentration of PEG8000 is 2% (w/v) and the concentration of Tween-20 is 6% (v/v). As shown in FIG. 15, the combination use of PEG8000 and Tween-20 can significantly shorten the threshold time of LAMP, and the effect is better than the single use of PEG8000 or Tween-20.

Figure 16:
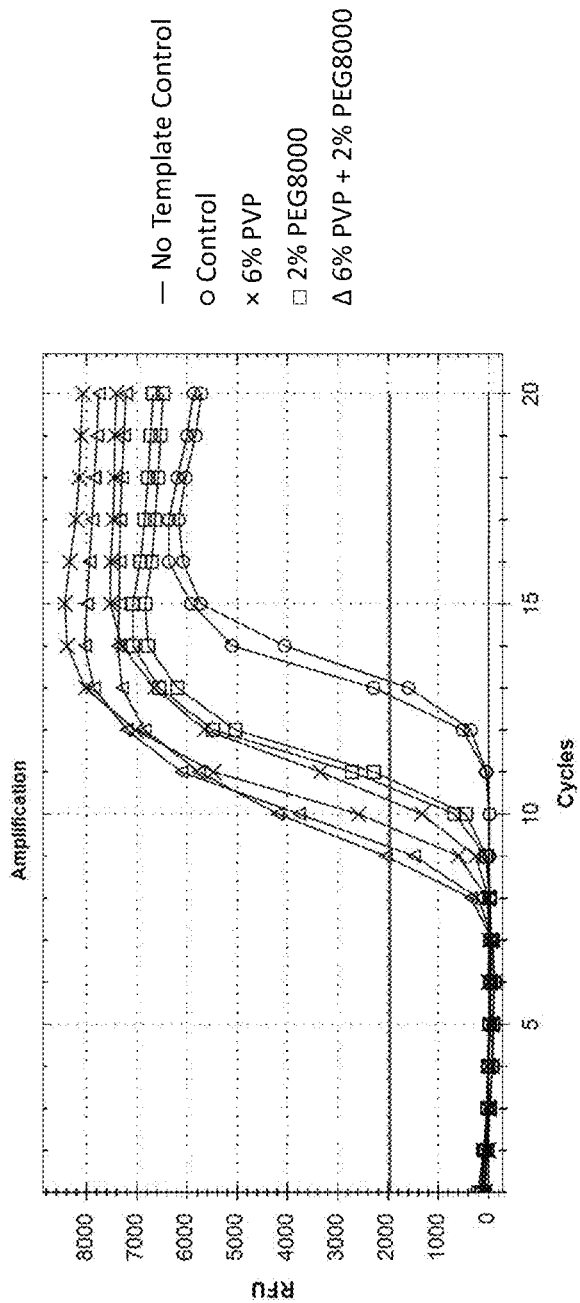
FIG. 16 shows the effects of individual or combination use of PVP and PEG8000 in LAMP reactions according to an embodiment of the present invention.

In an embodiment, PVP and PEG8000 were used as a combination of additives, wherein the concentration of PVP is 6% (w/v) and the concentration of PEG8000 is 2% (w/v). As shown in FIG. 16, the combination use of PVP and PEG8000 can significantly shorten the threshold time of LAMP, and the effect is better than the single use of PVP or PEG8000.

Figure 17:
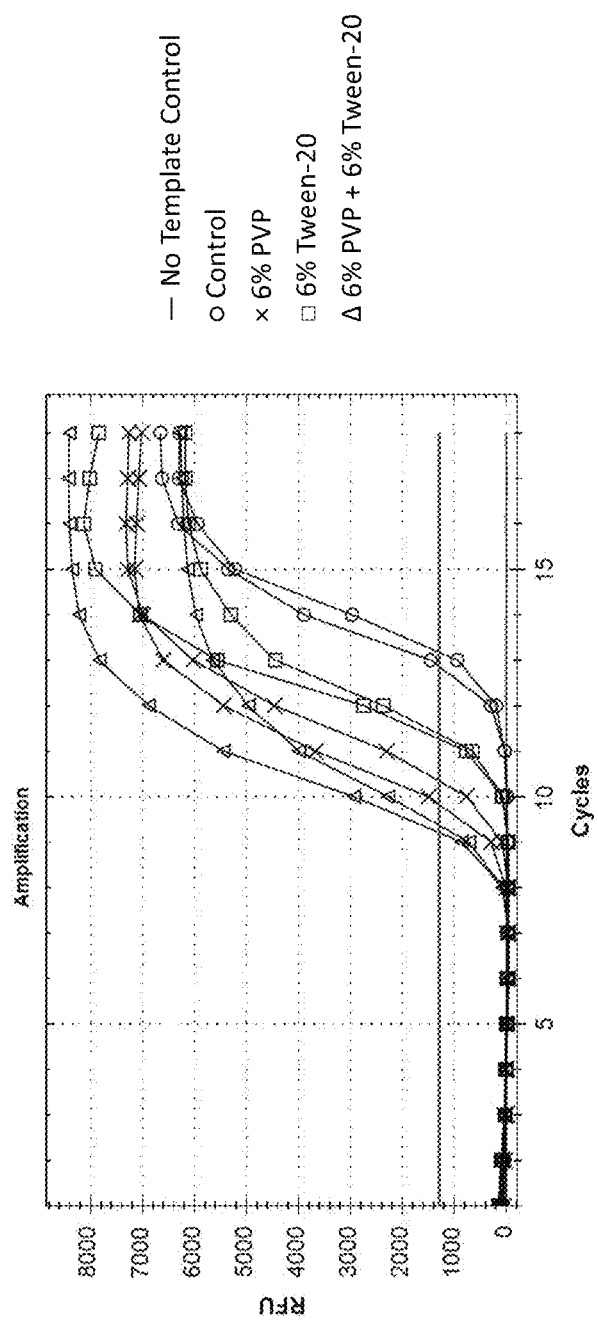
FIG. 17 shows the effects of individual or combination use of PVP and Tween-20 in LAMP reactions according to an embodiment of the present invention.

In an embodiment, PVP and Tween-20 were used as a combination of additives, wherein the concentration of PVP is 6% (w/v) and the concentration of Tween-20 is 6% (v/v). As shown in FIG. 17, the combination use of PVP and Tween-20 can significantly shorten the threshold time of LAMP, and the effect is better than the single use of PVP or Tween-20.

For the above embodiments for the combination uses of additives, although the combination effect was shown with one specific concentration of each additive, it is noted that any concentration within the workable concentration range of each additive has combinational effect.

Figure 18:
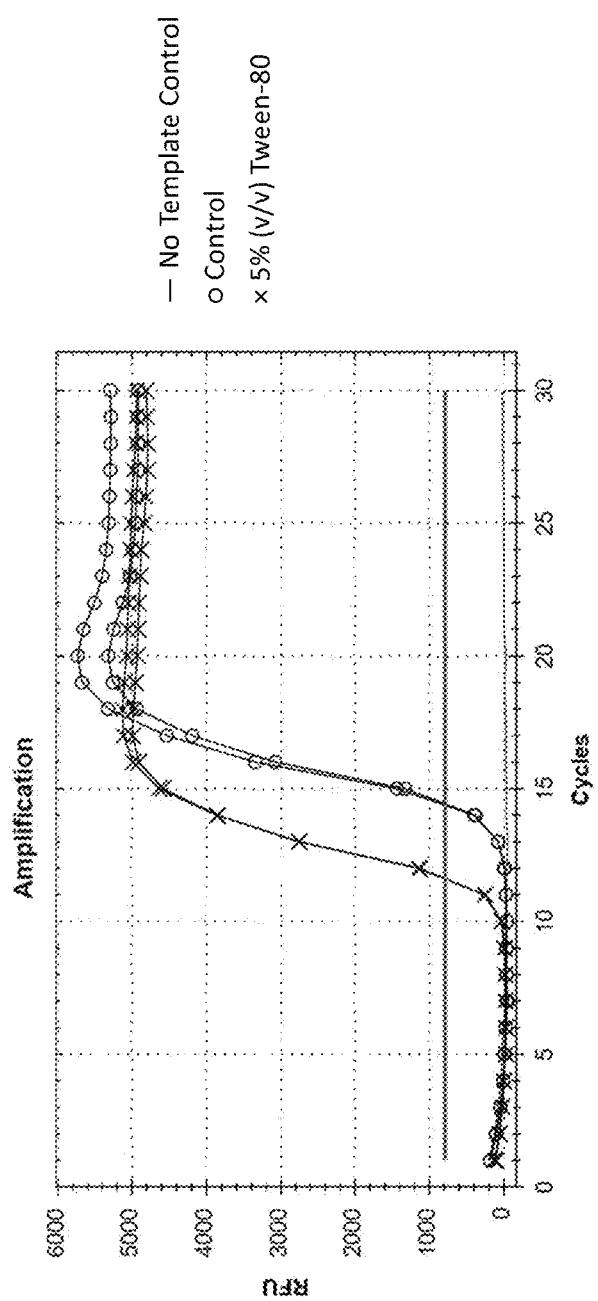
FIG. 18 shows the effect of individual use of Tween-80 in LAMP reactions according to an embodiment of the present invention.

In an embodiment, Tween-80 was used as an individual additive, and the tested concentration was up to 5% (v/v). It was found that the use of Tween-80 can shorten the threshold time of LAMP in a concentration range of 0.5-5% (v/v), preferably 2-5% (v/v), as shown in FIG. 18.

Figure 19:
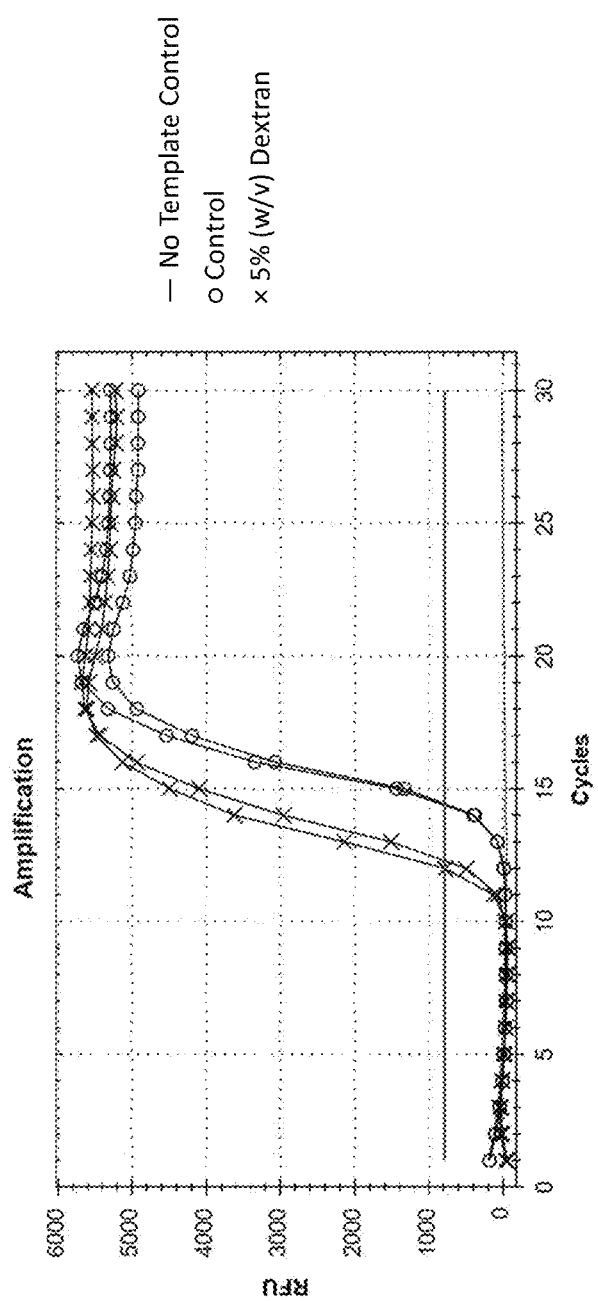
FIG. 19 shows the effect of individual use of Dextran in LAMP reactions according to an embodiment of the present invention.

In an embodiment, Dextran was used as an individual additive, and the tested concentration was up to 5% (w/v). It was found that the use of Dextran can shorten the threshold time of LAMP in a concentration range of 0.5-5% (w/v), preferably 2-5% (w/v), as shown in FIG. 19.

Figure 20:
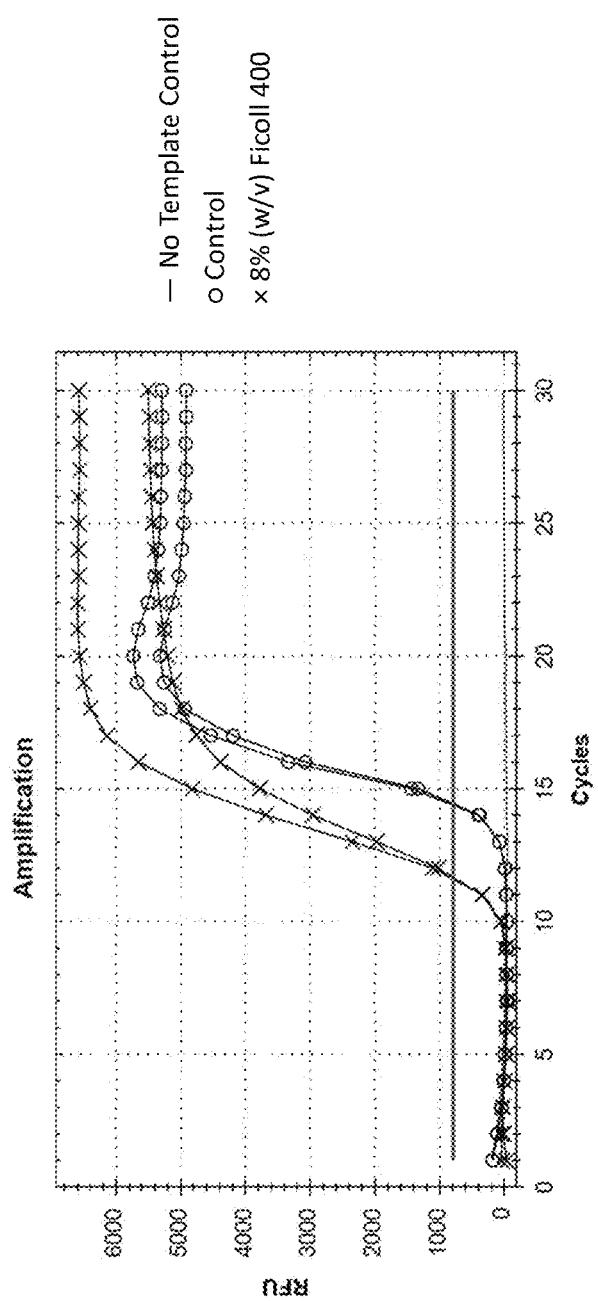
FIG. 20 shows the effect of individual use of Ficoll 400 in LAMP reactions according to an embodiment of the present invention.

In an embodiment, Ficoll 400 was used as an individual additive, and the tested concentration was up to 8% (w/v). It was found that the use of Ficoll 400 can shorten the threshold time of LAMP in a concentration range of 0.5-8% (w/v), preferably 5-8% (w/v), as shown in FIG. 20.

Figure 21A:
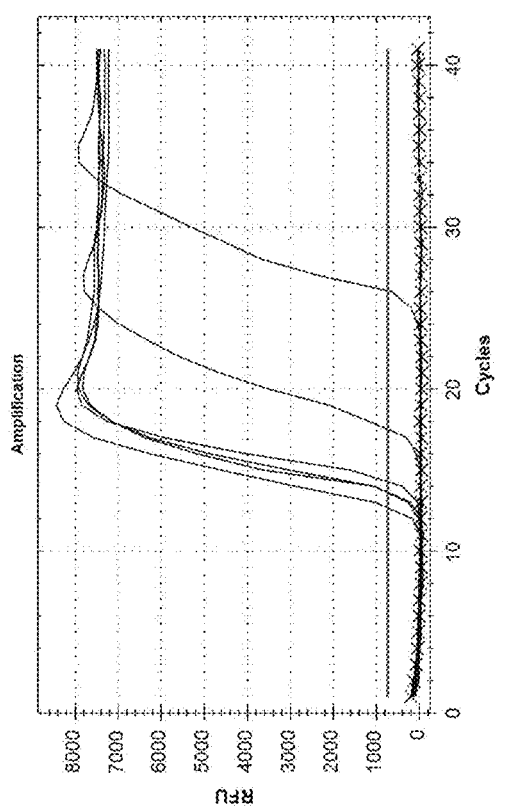
FIGS. 21A and 21B show the effect of combination use of BSA and EGTA in LAMP reactions for detecting low copy of template.
Figure 21B:
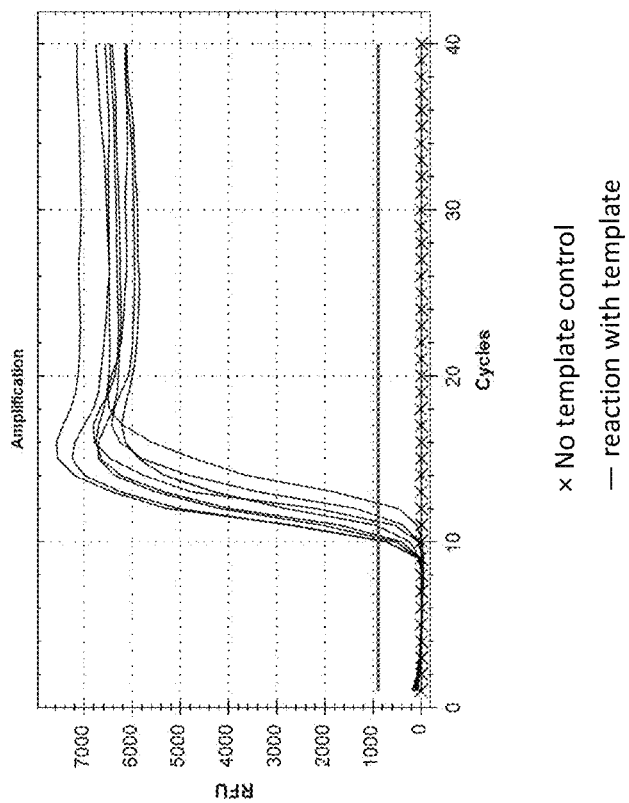

Besides, the present invention also tests if the detection of low copy of template can be enhanced by the additive. In an embodiment, LAMP was performed with the combination use of BSA and EGTA, and the result is shown in FIGS. 21A and 21B. As shown in FIG. 21A, without any additives, 6 out of 7 repeats of 40 copies of plasmid DNA were amplified. While as shown in FIG. 21B, with 2% (w/v) BSA and 2 mM EGTA in the reaction, 8 repeats of 20 copies of plasmid DNA were all amplified with a shorter threshold time and better repeatability. Therefore, the combination use of BSA and EGTA in LAMP can consistently detect low copy of template and also enhance the detection.

Figure 22:
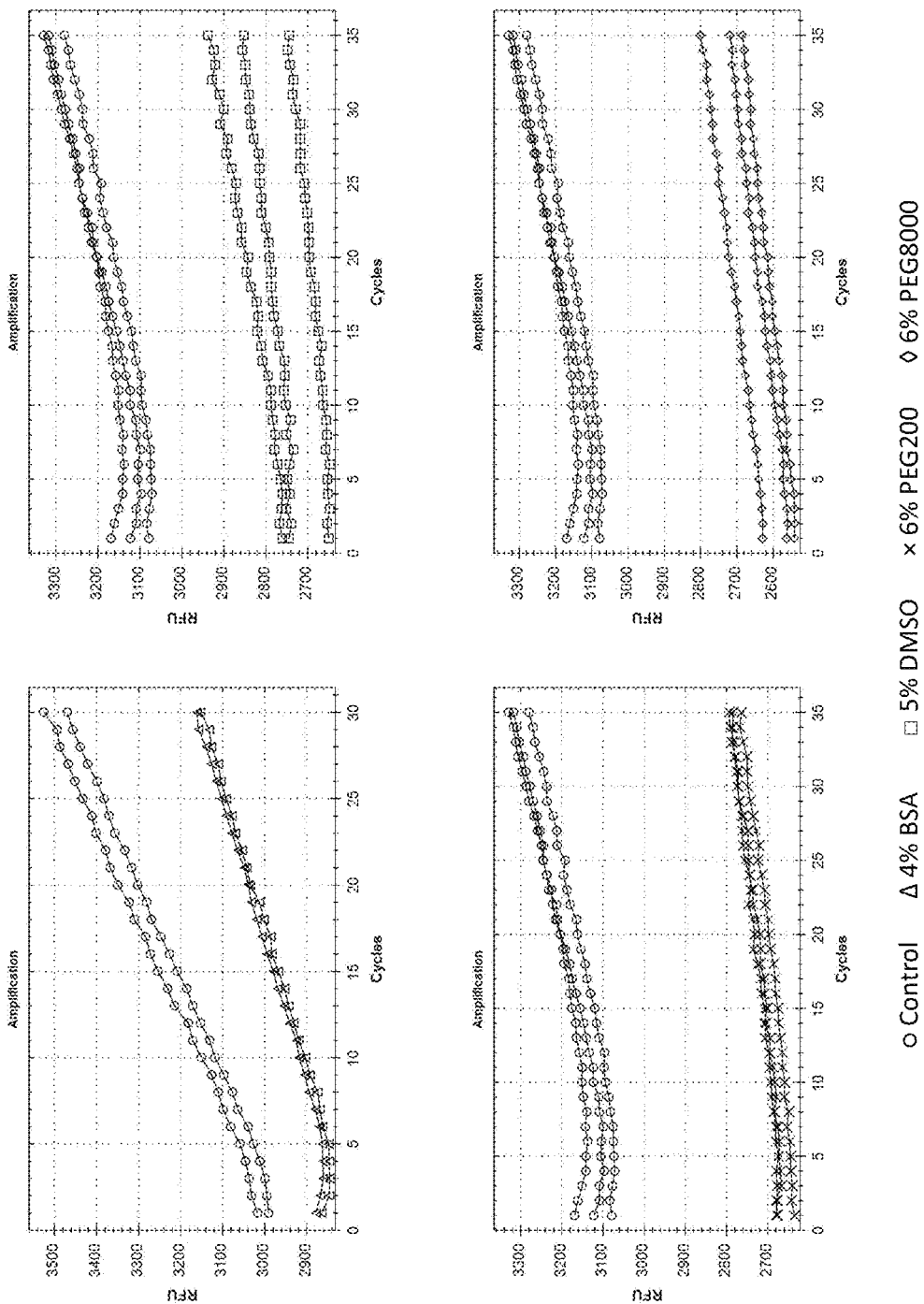
FIG. 22 shows the effects of individual uses of BSA, DMSO, PEG200 or PEG8000 in LAMP reactions for reducing template-independent background amplification.

On the other hand, the present invention further tests if the additive can reduce template-independent background amplification of LAMP primers. LAMP reactions were set up using 1.6 μM BIP primer without template in a buffer containing 20 mM Tris, pH 8.8 (25° C.), 50 mM KCl, 10 mM (NH$_4$)$_2$SO$_4$, 2 mM MgSO$_4$, and 0.1% (v/v) Tween-20, supplemented with additional 6 mM MgSO$_4$, 1.4 mM dNTPs, and optional additive composition. Reactions were all 25 μl, contained 8 U Bst polymerase (NEB M0538L), and were incubated at 67.4° C. Fluorescence signal was read every one minute. The result is shown in FIG. 22, which shows raw data of fluorescence measurement in Bio-Rad CFX96™ with presence of EvaGreen dye (Biotium) without threshold or baseline subtraction to show the non-specific background amplification.

In an embodiment, LAMP reactions were performed with an individual additive of 4% (w/v) BSA, 5% (v/v) DMSO, 6% (v/v) PEG200 or 6% (w/v) PEG8000. As shown in FIG. 22, the single use of BSA, DMSO, PEG 200 or PEG8000 can reduce template-independent background amplification of LAMP primers.

From the above, the present invention provides various additive compositions for enhancing LAMP reactions. The additive includes but not limited to EDTA, EGTA, BSA, DMSO, nonionic surfactants (such as Tween-20, Tween-21, Tween-40, Tween-60, Tween-61, Tween-65, Tween-80, Span 20, Span 40, Span 60, Span 80, Span 83, Span 85 and Span 120), and polymers (such as PEG, PVP, Dextran and Ficoll), and the additive composition used in LAMP reactions includes at least one of the above mentioned additives and may be any combination use of the additives. In other words, the above mentioned additives may be singly or combinationally used in LAMP reactions, and the number of additives used in LAMP reactions may be one, two, three or any other number.

In some embodiments, the combination use of additives has better effect than the single use of additive. For example, the additive composition may include a first additive and a second additive, wherein the first additive is selected from the group consisting of EDTA, EGTA and a combination thereof, and the second additive is selected from the group consisting of BSA, DMSO, nonionic surfactants, polymers and a combination thereof. Alternatively, the first additive is a polymer selected from the group consisting of PEG, PVP, Dextran, Ficoll and a combination thereof, and the second additive is selected from the group consisting of BSA, DMSO, nonionic surfactants and a combination thereof.

In some embodiments, the single use of additive also has effect for enhancing LAMP reactions. For example, the single additive is selected from the group consisting of EGTA, PVP, Dextran, Ficoll and Tween-80.

Using the additive compositions of the present invention in LAMP reactions has the advantage of reducing threshold time of positive samples. According to the above embodiments, the present invention significantly shortens the threshold time for LAMP amplification, allowing a faster detection of positive samples. Moreover, the present invention is able to greatly reduce template-independent background amplification of primers, allowing a clearer differentiation of positive samples from negative samples. In other words, the present invention lowers the level of non-specific background amplification. Further, the present invention allows the detection of lower copy number of target DNA consistently, and thus has better reaction consistency.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A reaction mixture comprising reaction components for performing a standard loop mediated isothermal amplification (LAMP) reaction and an additional LAMP-specific additive composition for reducing a threshold time for a positive sample and reducing template-independent background amplification, wherein the LAMP-specific additive composition comprises:
   a first additive selected from the group consisting of ethylenediaminetetraacetic acid (EDTA), ethylene glycol tetraacetic acid (EGTA) and a combination thereof; and
   a second additive selected from the group consisting of bovine serum albumin (BSA), dimethyl sulfoxide (DMSO), nonionic surfactants, polymers and a combination thereof.

2. The reaction mixture according to claim 1, wherein a concentration of EDTA is 0.1-1.5 mM.

3. The reaction mixture according to claim 1, wherein a concentration of EGTA is 0.1-3 mM.

4. The reaction mixture according to claim 1, wherein a concentration of BSA is 0.5-10% (w/v).

5. The reaction mixture according to claim 1, wherein a concentration of DMSO is 0.5-7% (v/v).

6. The reaction mixture according to claim 1, wherein the nonionic surfactants include Tween-20, Tween-21, Tween-40, Tween-60, Tween-61, Tween-65, Tween-80, Span 20, Span 40, Span 60, Span 80, Span 83, Span 85 and Span 120.

7. The reaction mixture according to claim 1, wherein a concentration of the nonionic surfactant is 0.5-6% (v/v).

8. The reaction mixture according to claim 1, wherein the polymers include polyethylene glycol (PEG), polyvinylpyrrolidone (PVP), Dextran and Ficoll.

9. The reaction mixture according to claim 8, wherein PEG includes PEG200 and PEG8000.

10. The reaction mixture according to claim 9, wherein a concentration of PEG200 is 0.5-8% (v/v), and a concentration of PEG8000 is 0.5-6% (w/v).

11. The reaction mixture according to claim 8, wherein a concentration of PVP is 0.5-10% (w/v).

12. The reaction mixture according to claim 8, wherein a concentration of Dextran is 0.5-5% (w/v).

13. The reaction mixture according to claim 8, wherein a concentration of Ficoll is 0.5-8% (w/v).

14. A reaction mixture comprising reaction components for performing a standard loop mediated isothermal amplification (LAMP) reaction and an additional LAMP-specific additive composition for reducing a threshold time for a positive sample and reducing template-independent background amplification, wherein the LAMP-specific additive composition is selected from the group consisting of:
   a first composition comprising a first additive selected from the group consisting of polyethylene glycol (PEG), polyvinylpyrrolidone (PVP), Dextran, Ficoll and a combination thereof, and a second additive selected from the group consisting of dimethyl sulfoxide (DMSO), nonionic surfactants and a combination thereof; and
   a second composition comprising a first additive selected from the group consisting of polyethylene glycol (PEG), Dextran, Ficoll and a combination thereof, and a second additive selected from the group consisting of bovine serum albumin (BSA), dimethyl sulfoxide (DMSO), nonionic surfactants and a combination thereof.

15. The reaction mixture according to claim 14, wherein PEG includes PEG200 and PEG8000.

16. The reaction mixture according to claim 15, wherein a concentration of PEG200 is 0.5-8% (v/v), and a concentration of PEG8000 is 0.5-6% (w/v).

17. The reaction mixture according to claim 14, wherein a concentration of PVP is 0.5-10% (w/v).

18. The reaction mixture according to claim 14, wherein a concentration of Dextran is 0.5-5% (w/v).

19. The reaction mixture according to claim 14, wherein a concentration of Ficoll is 0.5-8% (w/v).

20. The reaction mixture according to claim 14, wherein a concentration of BSA is 0.5-10% (w/v).

21. The reaction mixture according to claim 14, wherein a concentration of DMSO is 0.5-7% (v/v).

22. The reaction mixture according to claim 14, wherein the nonionic surfactants include Tween-20, Tween-21, Tween-40, Tween-60, Tween-61, Tween-65, Tween-80, Span 20, Span 40, Span 60, Span 80, Span 83, Span 85 and Span 120.

23. The reaction mixture according to claim 14, wherein a concentration of the nonionic surfactant is 0.5-6% (v/v).

24. A reaction mixture comprising reaction components for performing a standard loop mediated isothermal amplification (LAMP) reaction and an additional LAMP-specific additive composition for reducing a threshold time for a positive sample and reducing template-independent background amplification, wherein the LAMP-specific additive composition consists of a single additive selected from the group consisting of ethylene glycol tetraacetic acid (EGTA), polyvinylpyrrolidone (PVP), Dextran, Ficoll and Tween-80.

25. The reaction mixture according to claim 24, wherein a concentration of EGTA is 0.1-3 mM.

26. The reaction mixture according to claim 24, wherein a concentration of PVP is 0.5-10% (w/v).

27. The reaction mixture according to claim 24, wherein a concentration of Dextran is 0.5-5% (w/v).

28. The reaction mixture according to claim 24, wherein a concentration of Ficoll is 0.5-8% (w/v).

29. The reaction mixture according to claim 24, wherein a concentration of Tween-80 is 0.5-5% (v/v).

* * * * *